United States Patent
Bjørgaas

Patent Number: 6,152,884
Date of Patent: Nov. 28, 2000

[54] METHOD AND INSTRUMENT FOR EXAMINATION OF HEART/ARTERIES USING MICROPHONES

[76] Inventor: Per Samuel Bjørgaas, P.O. Box 71, N-4001 Stavanger, Norway

[21] Appl. No.: 09/171,559
[22] PCT Filed: Apr. 16, 1997
[86] PCT No.: PCT/NO97/00101
§ 371 Date: Oct. 19, 1998
§ 102(e) Date: Oct. 19, 1998
[87] PCT Pub. No.: WO97/39678
PCT Pub. Date: Oct. 30, 1997

[30] Foreign Application Priority Data

Apr. 25, 1996 [NO] Norway ................................. 961646
Apr. 16, 1997 [NO] Norway ................................. 971733

[51] Int. Cl.⁷ .............................. A61B 5/02; A61B 7/00
[52] U.S. Cl. .......................... 600/528; 600/513; 600/586
[58] Field of Search .................................... 600/528, 586, 600/513

[56] References Cited

U.S. PATENT DOCUMENTS

| | | |
|---|---|---|
| 4,628,939 | 12/1986 | Little et al. |
| 4,672,977 | 6/1987 | Kroll ....................... 600/528 |
| 5,025,809 | 6/1991 | Johnson et al. |
| 5,365,937 | 11/1994 | Reeves et al. ............. 600/528 |
| 5,458,116 | 10/1995 | Egler . |
| 5,718,227 | 2/1998 | Witlin et al. ............. 600/586 |
| 5,844,997 | 12/1998 | Murphy, Jr. |

FOREIGN PATENT DOCUMENTS

| | | |
|---|---|---|
| 38 30 412 | 3/1990 | Germany . |
| 42 44 646 | 6/1994 | Germany . |
| WO 94/27497 | 12/1994 | WIPO . |

OTHER PUBLICATIONS

Chihara, Kuni Hiro et al, "Construction on Imaging Method of Diagnostic Information of Heart Sounds", *The Transactions of the IEEE of Japan*, vol. E, 63, No. 9, Sep. 1980, pp. 670–671.

Primary Examiner—Carl H. Layno
Attorney, Agent, or Firm—Mathews, Collins, Shepherd, & Gould, P.A.

[57] ABSTRACT

A method for examination of heart/arteries to obtain information in form of measurement results as a basis for exact diagnosis, where electrodes are placed on suitable areas of the body to provide signals, and where, by signal processing, a three-dimensional ECG vector cardiogram is obtained, which is illustrated by a three-dimensional picture of the heart. According to the invention, sound from—say—three places over a period of time is registered, as the signal fluctuations which are synchronized with the heartbeats are calculated, so that sounds from other sources i.e. intestines, lungs are eliminated. The heart's arteries electromagnetic movements are illustrated in order to visualize its pathology. The instrument comprises preferably three or more microphones in addition to poles for electromagnetic registration, attached to a preferably battery operated converter, arranged to receive pulses and send on signals to a computer, the computer being programmed to—on the basis of the different part-diversions—calculate and screen a three-dimensional picture of the depolarization (the electromagnetic movement in the heart).

3 Claims, 1 Drawing Sheet

६,१५२,८८४

METHOD AND INSTRUMENT FOR EXAMINATION OF HEART/ARTERIES USING MICROPHONES

BACKGROUND OF THE INVENTION

1. Field of the Invention

This invention deals with a method of examining of heart/arteries in order to obtain information facilitating exact diagnosis, where electrodes, poles and microphones etc. are placed in easily recognised positions on the human body, and, where is developed a three dimensional picture of the movement of the heart varying according to time. The invention also concerns itself with an instrument for the same purpose.

With the invention one has generally aimed at arrival of a method and instrument for the given use, making it possible to discover thickening of the arteries earlier than can be achieved with existing methods and instruments, particularly as one, with this invention, work with simpler and cheaper means than before.

2. Description of Related Art

Experience tells us that physicians in general practice only refer patients to a cardiologist when more serious symptoms are evident or where there is a strong suspicion of heart/artery failure. Such suspicions can be based on family-history, bloodchemistry or a traditional electrocardiogram. The cardiologist will carry out a comprehensive programme to ascertain the patient's artery-system. Stress-electrocardiography is used, where the patient cycles and comes under strain while concurrently a traditional electro-cardiogram is registered.

Another form of examination uses an echo-doppler led towards the heart and the heart stream so that movements over the valves can be measured. But it is difficult to find other arteries. Good access to the throat arteries exist but the smaller puls-arteries are harder to locate. The third method a cardiologist uses is a very recource-intensive form, angiography, contrast fluid is pumped into the bloodstream and the arteries shown, using X-rays.

To the present invention's general purpose belongs revealing of patients needing angiography-based treatment with duct-out-blocking/dilating of the arteries to the heart and possible dilation of other arteries i.e. those to the kidneys.

It is known that dataprogrammes based on a traditional electrocardiogram give rise to a vector-cardiogram.

U.S. Pat. No. 5,458,116 deals with a display-system and a process previously mentioned, for display of a threedimensional vector-cardiogram. According to this known technique six electrodes are placed on the body and by signal processing a 3-dimens. vector-cardiogram varying in tune, is produced. It is modelled as a vector in the 3-dim.room. According to this U.S. patent the vector-cardiogram represents the total electrical activity to the heart.

DE 38 30 412 concerns a diagnostic apparatus which registers sound in the body. Many microphones are used, thus making it possible to locate the origin of the sound. Thereafter a picture is made of the area from where the sound came. This is planned for use in connection with diagnosis of the intestine. This publication shows and describes, however, a diagnostic device used on intestines rather than for heart an arteries. In accordance with the invention at present under consideration, the sound which exists simultaneously with a heartbeat over a period, is registered, in that the signals which are synchronized with the heartbeats are registered and accumulated, so eliminating sounds from other soundproducing sources, as. F.ex. intestines and lungs.

With this method sound-ECG can with advantage, combine with ultrasound so that an exact measure of the thickness of the heartwall is achieved.

SUMMARY OF THE INVENTION

An instrument which can be used advantageously by this method in heart-/artery examinations, comprise microphones and poles for electromagnetic registration, which are placed on easily recognisable points on the body and, for example, battery-operated converter for reception of pulses (pulsation) from the electrodes and managed in a way which will send signals on to a computer. This, in turn, calculates a 3-dim.picture of the heart's depolarisation (electromagnetic movement in the heart), based on a summary of the varied, derivations, simultaneously positioning a picture showing where different sounds come from in the circulation.

Based on the collected data the computer can calculate and show on the screen a 3-dim.illustration of the activity of the heart, possible thickening of the arteries and valve failure. Areas which have been exposed to infarct of the heart or where the blood stream is reduced, will also show in the illustration.

The instrument, according to the invention, is not likely to compare with the echo-doppler in measuring accuracy, but will be considerably simpler to use and at the same time, much cheaper to produce.

Originally electro-cardiograms were displayed as vector-cardiograms. However, such diagrams are difficult to interpret. One embarked therefore on a solution with twelve leads, so that an experienced physician could interpret where pathology existed. Typical sources of failure consisted of misplacement of the electrodes, so that repeated registrations where inexact. A computer calculated and screened 3-dim. picture is better able to illustrate the function of the heart and make the interpretation easier for doctors in general practice. The instrument according to the invention, is first and foremost intended for use in general practice, where the doctor can diagnose heart conditions and follow up heart-patients by better and cheaper means. The instrument should be produced at least for the same price as an electro-cardiograph.

DETAILED DESCRIPTION

Figure 1:
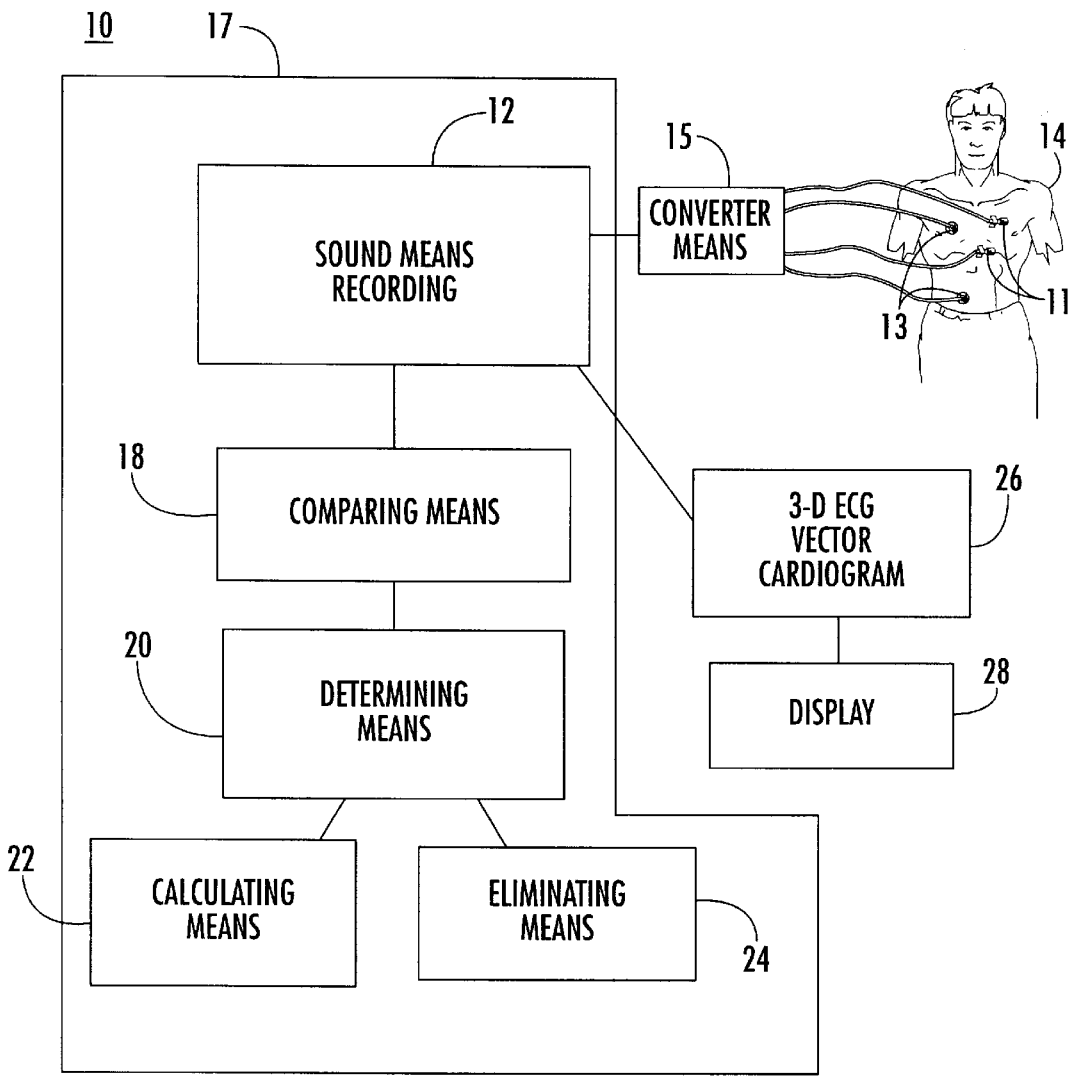
FIG. 1 is a schematic diagram of an instrument for examining the heart and arteries in accordance with the teachings of the present invention.

FIG. 1 schematically illustrates instrument 10 in accordance with the teachings of the present invention. Microphones 11 and electrodes 13 for electromagnetic registration, are placed on easily recognizable points on body 14 and converter 15 which can be, for example, battery-operated for reception of pulses (pulsation) from electrodes 13 is used for converting same and sending signals of the converted pulses to computer 17. Pulses computer 17, in turn, calculates a 3-dimensional ECG vector cardiogram 26 of the heart's depolarization (electromagnetic movement in the heart), based on a summary of the varied, derivations, simultaneously positioning an illustration of the 3-dimensional ECG vector cardiogram showing where different sounds come from in the circulation. Based on the collected data computer 17 can calculate and show on display 28 a 3-dimensional illustration of the activity of the heart.

As mentioned, the procedure is, according to the invention, based on placement of 6–8 electrodes 13 on easily recognisable and reproduceable areas, as, for instance, in the middle of the breast-bone and exactly between the shoulderblades. This ensures calculations of the heart's action and gets it 3-dim.illustrated. Registration of signals is interrupted after ½–1 min, when the computer calculates the mean fluctuation, in that one with considerable accuracy can ascertain changes in the heart.

Sound will also be registered over a period of time with sound recording means 12, parallel with ECG, after which one calculates signals which are synchronized with the heartbeats. Consequently, sounds from other sources—intestines and lungs and compared with comparing means 18—and after "eliminated" insert—by determining the repeatability of the sound signals and non repeatability of the sound signals with determining means 20—are eliminated. With the use of high-frequency and low-frequency registration area, one will be able to discover blockages otherwise not audible with a stethoscope. Because of sound's travelling-speed in tissues, one can with the help of three or four differently placed microphones 11 receive the necessary information on the origin of the sounds. This can be built into the abovementioned 3-dim.picture and one will have illustrated which arteries have incipient blockage.

In sound-registration this happens preferably at three to four different places, in that the registrations coordinate with the beats of the pulse, so that one only takes up the sounds attached to the heartbeats. One accumulates up to 100 beats so that undesired sounds are filtered away. One can later divide it into different frequency-areas and there compare with comparing means 18 decided frequency-areas from at least three different microphones 11. The computer 17 calculates the distance between the microphones and the area from where the sound originally came, from a displacement of the time of the complex. The computer 17 can also be programmed to locate this stenose-sound, i.e. blocking sound, for example the right throat artery, left kidney or the heart-artery with calculating means 22 to calculate the possible location of a contraction.

Supplementary information under the vector-programme, accumulating the ECG signals using the same principle, small micro-derivations can be achieved, something which within medicine are called ST-complexes. It appears, according to latest research, that this can give safer indication of some heart-conditions, achieved by accumulating several heartbeats above each other, so that background noise is filtered away eliminating means 24 for eliminating non regularly repeated sound signals.

In addition to known electrical registration will, according to the invention, the registration of sound, in a sufficiently broad spectrum, come with the assistance of one or more sets of preferably three or four microphones 11, which can be equipped, formed and arranged to register usual, electrical activity.

By using a limited number, or a relatively small number, of registration points, and by placing them on areas easy to reproduce, the registration points can be placed in exactly the same area on the patient's next visit.

The registration itself can stretch over a minute or two-three minutes, depending on the required degree of accuracy and of, possibly, the arythmia tendency (irregular heart-activity). The computer 17 then calculates the sound-picture from different areas. This is also synchronized, co-ordinated with the heart-action, to ensure that all undesired noise in form of skin-rubbing, breathing, intestinal sounds etc. are filtered out, and only the sounds relating to the activities of the heart, remain. This will provide an image of the blood-circulation, and the heart sounds from the different registrations will be compared, so that sounds with certain frequencies and certain strengths can be localised because of a time-displacement which will then indicate the distance from the microphone to the stenosis (point of thickening in the artery). Because the time-displacement from the different registrations vary, one can ascertain from where this turbulence comes.

A picture is formed, illustrating the movement of the heart through one heartbeat so that an average heartbeat is reproduced, where one sees the deviation from a normal heartbeat. In the same picture will also be shown those areas where thickenings are found. As a point of reference the well-known aortavalve can be used. This makes a decidedly loud noise, something which will be easy to locate, geographically. It moves little in relation to the rest of the heart-musculature and is recognisable in most patients.

As one can shift the frequencies of the stenose-sounds, one can possibly obtain sounds from what one calls the small circulation, heart—lungs—back to heart.

What is claimed is:

1. An instrument for examining the heart and arteries comprising:

sound recording means for recording sound from two or more mutually different measuring points on a patient's body as sound signals;

comparing means for comparing said sound signals received from a measuring point other than the measuring point assigned the heart region with sound signals from the heart region;

determining means for determining the possibly regularly repeatability of said sound signals and non regularly repeatablity of said sound signals;

calculating means for calculating a possible location for a contraction from said sound signals; and eliminating means for eliminating said non regularly repeated sound signals as non interesting sound signals, wherein said sound recording means comprise two or more microphones assignable to mutually different measuring points on the patient's body.

2. The instrument of claim 1, further comprising:

electrodes for electromagnetic recording assignable to said different measuring points on said patient's body; and converter means connected to said electrodes for converting pulses received from said electrodes into electromagnetic signals, said converter means being programmed to calculate and display on the basis of various partial diversions;

means for producing a three-dimensional ECG vector cardiogram from said sound signals and said electromagnetic signals; and means for illustrating said three-dimensional cardiogram to provide a three-dimensional image of the heart.

3. The instrument of claim 2, wherein a three-dimensional image of the heart depolarization is illustrated and at the same time said location of said contraction is illustrated.

* * * * *